United States Patent

Källback

[11] Patent Number: 5,928,953
[45] Date of Patent: Jul. 27, 1999

[54] METHOD OF ANALYSIS AND EQUIPMENT THEREFORE

[76] Inventor: Patrik Källback, Fadderortsgatan 3, SE-654 66 Karlstad, Sweden

[21] Appl. No.: 08/990,320

[22] Filed: Dec. 11, 1997

[30] Foreign Application Priority Data

Dec. 12, 1996 [SE] Sweden .................................. 9604566

[51] Int. Cl.⁶ .................................................. G01N 35/10
[52] U.S. Cl. ........................... 436/52; 436/174; 436/179; 436/180; 422/68.1; 422/81; 422/103
[58] Field of Search .................................. 436/43, 52, 53, 436/174, 179, 180; 422/68.1, 81, 82, 103

[56] References Cited

U.S. PATENT DOCUMENTS

| | | | |
|---|---|---|---|
| 3,954,411 | 5/1976 | Snyder | 422/82 |
| 4,022,575 | 5/1977 | Hansen et al. | 422/81 |
| 4,036,062 | 7/1977 | Cruzan | 43/422 GC |
| 4,101,275 | 7/1978 | Taguchi et al. | 422/81 |
| 4,231,990 | 11/1980 | Jottier | 422/100 |
| 4,314,824 | 2/1982 | Hansen et al. | 422/81 |
| 4,424,276 | 1/1984 | Clark et al. | 436/50 |
| 4,645,647 | 2/1987 | Yoshida et al. | 422/81 |
| 4,865,992 | 9/1989 | Hach et al. | 436/51 |
| 4,873,057 | 10/1989 | Robertson et al. | 422/75 |
| 5,055,260 | 10/1991 | Roberge et al. | 422/62 |
| 5,139,956 | 8/1992 | Schick et al. | 436/52 |
| 5,192,509 | 3/1993 | Surjaatmadja et al. | 422/75 |
| 5,230,863 | 7/1993 | Salpeter | 422/67 |
| 5,240,681 | 8/1993 | O'Lear et al. | 422/82 |
| 5,393,492 | 2/1995 | Di Martino et al. | 422/62 |
| 5,407,832 | 4/1995 | Hayashibe et al. | 436/74 |
| 5,447,692 | 9/1995 | Keenan et al. | 422/116 |
| 5,679,575 | 10/1997 | Kubota et al. | 436/49 |

*Primary Examiner*—Long V. Le
*Attorney, Agent, or Firm*—Kilpatrick Stockton LLP

[57] ABSTRACT

In connection with a method for determination of the content of at least some substance which is solved in a liquid, is used a measuring device, which is arranged to detect the character of a physical magnitude of the liquid, which physical magnitude is related to the content of the present substance, when the liquid has been treated with an adequate reagent. A volume of the reagent is measured, which volume corresponds to a defined length of a line, in which the reagent is transported, whereafter the measured volume is incorporated in a closed loop (1) in which the measuring device (26) is included, whereby the reagent volume which is incorporated in the measuring loop initially is essentially unmixed with the sample liquid and forms a section (X) in the line of the loop, which for the rest is filled with sample liquid and whereby the length of said section corresponds to or is in direct proportion to said length of the line in which the reagent is transported before it is incorporated into the loop. The sample liquid and the reagent is, thereafter, transported around in the measuring loop by means of a pump (25) which is included in the measuring loop, until the sample liquid and the reagent is thoroughly mixed in the measuring loop, whereafter the measuring device registers the content of the compound in question.

8 Claims, 3 Drawing Sheets

METHOD OF ANALYSIS AND EQUIPMENT THEREFORE

TECHNICAL FIELD

The invention relates to a method in connection with determination of the content of at least some substance which is solved in a liquid, whereby a measuring device is used, which is arranged to detect the character of a physical magnitude of the liquid, which physical magnitude is related to the content of the present substance, when the liquid has been treated with an adequate reagent. The invention relates, particularly, to a calorimetric method of analysis.

SHORT DESCRIPTION OF THE INVENTION

An object of the invention is to provide a method of analysis, which only demands small amounts of sample and amounts of reagent for analysis, which enables continuous analyses and which also fulfils the other requirements on modern, chemical, quantitative analysis methods and analysis equipment. Of these requirements it can be mentioned that the equipment shall be constructed for short response and stabilising times and high accuracy and large reproducibility. The equipment shall, moreover, be able to be built up from a few standard components and be constructed to be easy to automatize, easy to clean through flushing with small volumes and have small consumption of chemicals, low operating costs and small dimensions.

These and other objects of the invention can be achieved through what is stated in the preceding independent patent claims.

Additional characters and aspects of the invention appear in the dependent claims and in the following description of a preferred embodiment.

SHORT DESCRIPTION OF THE DRAWINGS

It will, in the following description of a preferred embodiment, be referred to the attached drawing figures, where FIGS. 1–5 schematically illustrates the equipment according to the preferred embodiment and different stages in the method of analysis.

DESCRIPTION OF A PREFERRED EMBODIMENT

Figure 2:
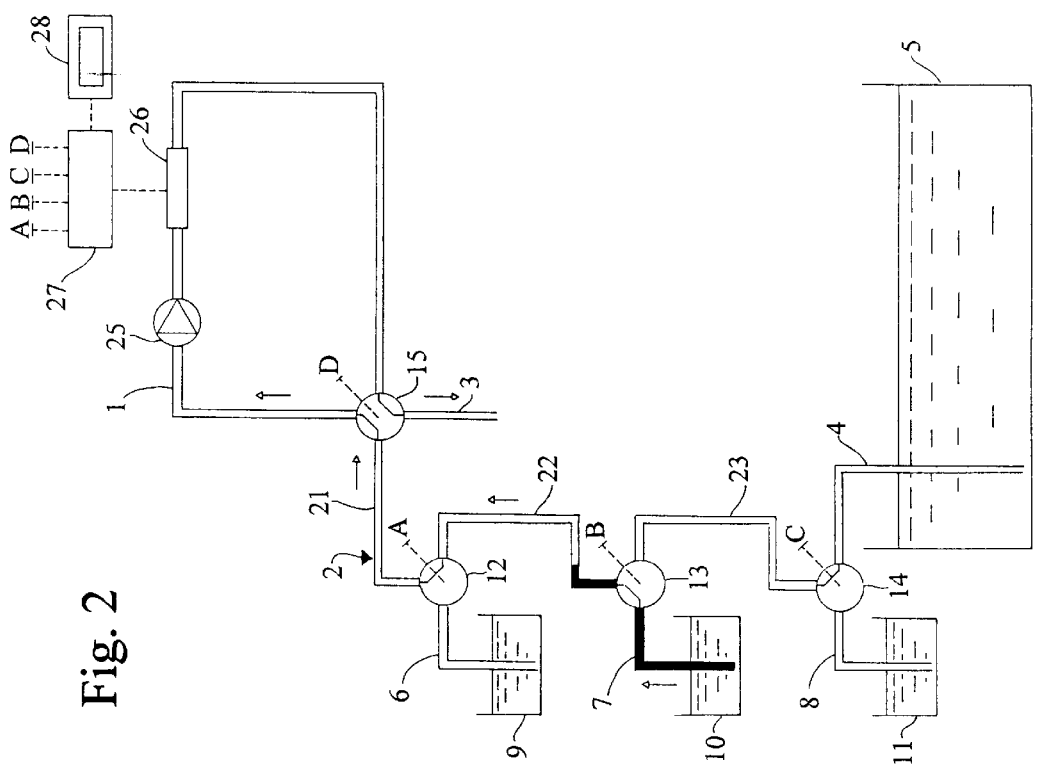

A measuring loop is, in the drawing figures, generally denoted with the digit 1 and a transport line with the digit 2. The transport line 2 consists of a first section 21, a second section 22 and a third section 23. A discharge conduit to the sink has been denoted 3. There is further, a connection line 4 to a sample liquid source 5 and connection lines 6, 7 and 8 to first, second and third reagent sources 9, 10 and 11, respectively. The sample liquid source 5 and the reagent sources 9–10 can, via the connection lines 4 and 6–8 be connected to the transport line 2, via first, second and third connection valves 12, 13 and 14, respectively. The connection valves are of three-way type. The transport line 2 and the discharge conduit 3 can, further, be connected to or disconnected from the measuring loop 1 by means of a four-way main valve 15.

In the measuring loop 1, there is a pump 25 and a member which is part of a photometrically operating measuring device 26, that is a measuring device which optically analyses the liquid which passes by the measuring member. The primary measurement test results are transmitted in the form of electrical impulses to a computer 27 for treatment and converting to readable measurement test results on a display 28 or on a printer or the like.

The computer 27, or some other automatic mechanism, is further arranged to control the connection valves 12, 13, 14 and the main valve 15. The valves are, more specifically, arranged to be time controlled with high accuracy.

The pump 25 in the measuring loop 1 consists of a displacement pump which gives a very stable flow in the measuring loop. This can be achieved by several different types of pumps, such as gear-driven pumps, peristaltic pumps (hose pumps), screw pumps, centrifugal pumps and impeller pumps. A pump which has proven to be very suitable is a gear-driven pump.

The lines in the measuring loop 1 and in the transport line 2 are made of hoses or tubes arranged to withstand underpressure or overpressure in the loop and in the transport line without their volume being measurably effected. Preferred inner diameters in the line system are 0.5–2.5 mm, preferably 1–2 mm and suitably 1.2–1.7 mm. Larger, as well as smaller diameters and cross-sectional areas are though conceivable. The same dimensions should though be used pervadingly in the greatest possible part of the line system, in order to avoid disturbing fluctuations in the flow characteristic and the diameter should be small in order to bring down the volume. The lines can be made of armoured or unarmoured hose of the type PTFE, KELF or PEEK, preferably PTFE, or of metal materials such as acidproof steel or titanium, preferably titanium. In the example which is illustrated, the inner diameter was 1.5 mm and the volume of the entire line system was about 7 ml.

The equipment comprises, in the shown embodiment of the equipment according to the invention, three connection valves 12, 13 and 14, which are connected in cascade and are connectable to three different reagent sources 9, 10 and 11. It should be realised that this only is one of several conceivable embodiments. The equipment could thus, in its simplest form, include only one single connection valve 12 for connection of transport lines to the sample liquid source and to a reagent source. In an equipment for testing of more substances in a liquid than three, can the number of cascade connected connection valves including connection lines, naturally also be more than three.

The use of the described equipment will now be explained further through the description of a conceivable application, namely the measuring of pH and the amount of free chlorine and the total amount of chlorine in swimming pool water.

Figure 1:
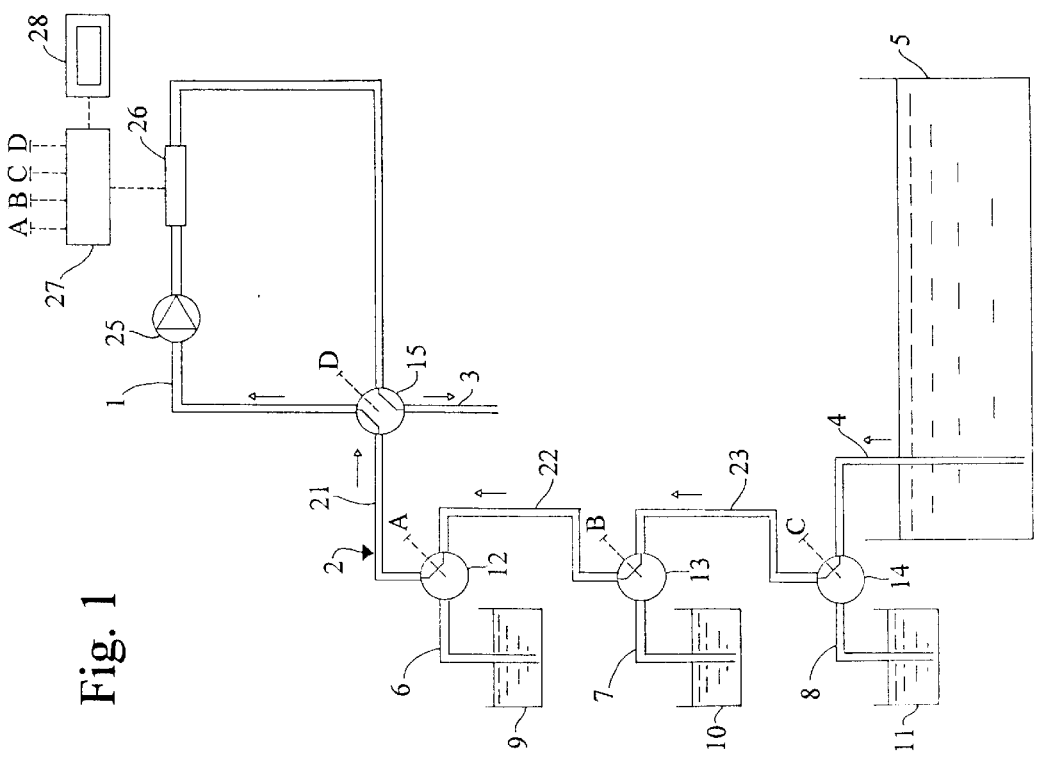

The method is started by sample liquid, that is bath-water in the present case, being led into the loop 1, from the sample liquid source 5 via the connection line 4, the connection valves 14, 13, 12 and the transport line sections 23 and 22 in-between, the continuing part 21 of the connection line 2 and the main valve 15, as is shown in FIG. 1. The sample liquid is drawn into the measuring loop 1 by means of the pump 25, in order to completely fill the measuring loop, all remains from previous measurements being flushed away, whereafter liquid is led out through the discharge conduit 3 to the sink.

Figure 3:
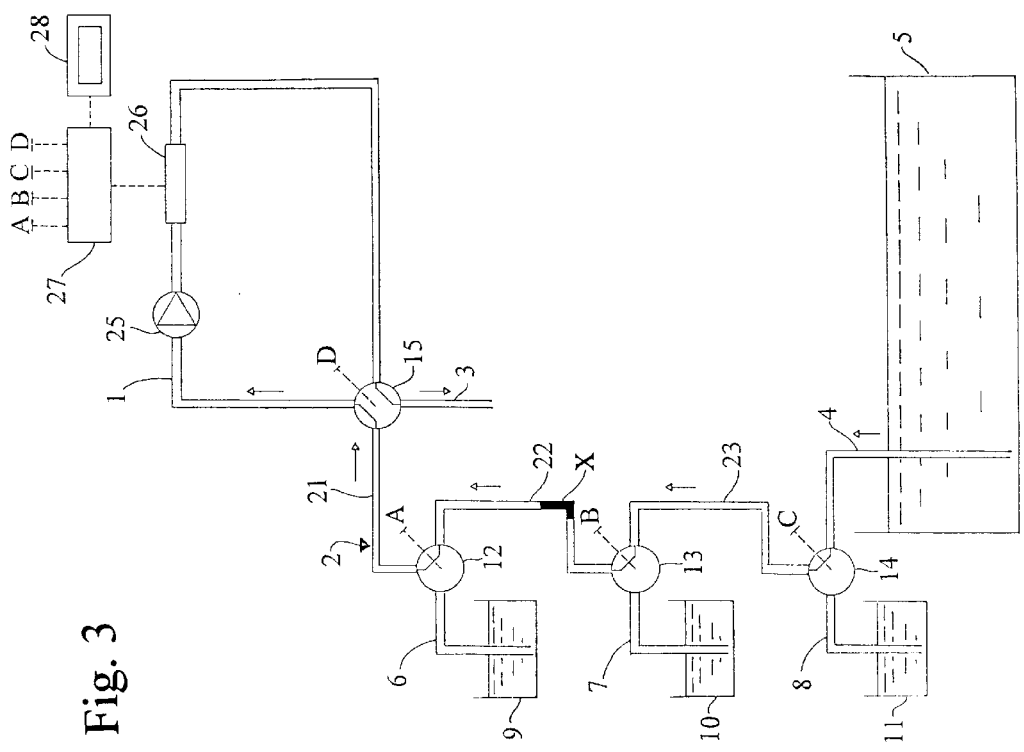
Figure 5:
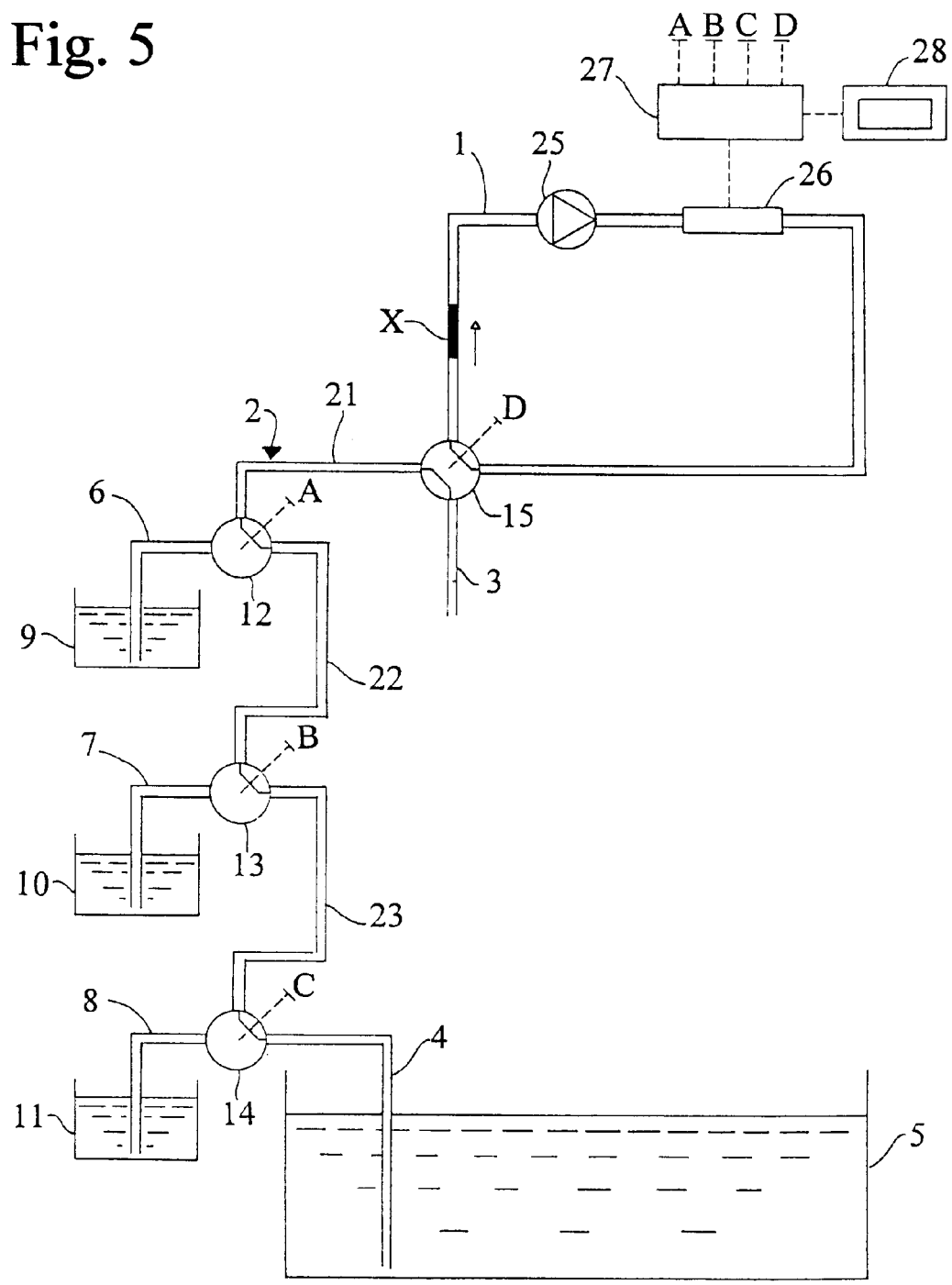

It is supposed that the first thing that is wished to be measured during the continuation of the method is the amount of free chlorine in the water. As reagent for such a measurement can be used DPD1, which is present in the reagent liquid source 10. A certain volume V of DPD1 is, thereby, led into the system via the connection line 7 and the connection valve 13, which is switched over to a position which connects the connection line 7 with the transport section 22 of the transport line 2. The connection valve 13 is kept in this position for a certain defined time interval, for example 0.25 s, which is controlled by the computer 27. The said reagent volume V=Q·t, not more than 100 μl though, corresponding to a length of the line which is about 50 mm, is during this time drawn into the transport line 2, where Q=flow velocity and t=the time interval that the valve 13 is open. The connection valve is, thereafter, returned to its normal position, in order to once again draw sample liquid into the transport line, FIG. 3. The amount of DPD1 forms a section X in the line and is drawn forward in the line by the pump 25, through the first connection valve 12, the line section 21 and the main valve 15, into the measuring loop 1, at the same time as sample liquid is replenishing from behind from the sample liquid source 5 and at the same time as sample liquid is fed out from the measuring loop 1 through the main valve 15 via the discharge conduit 3 to the sink.

Figure 4:
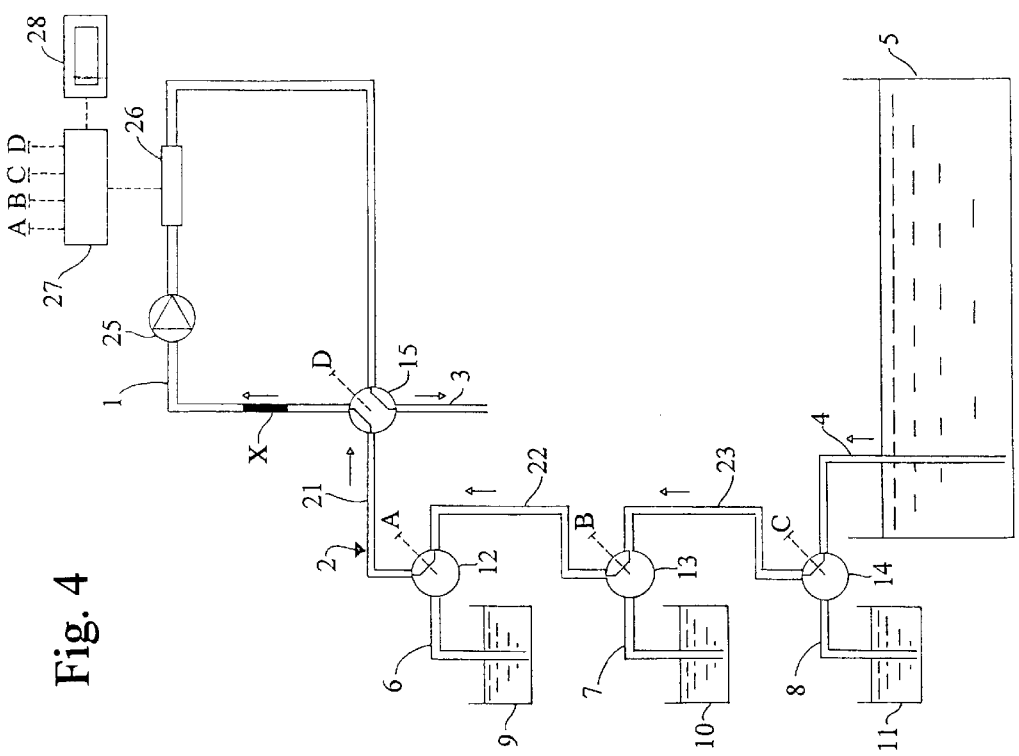

The main valve 15 is, when the section X, which consists of DPD1, has entered the measuring loop 1, FIG. 4, switched to close the measuring loop 1. This will take about 2 s from the valve 13 being switched to its normal position after having led the intended amount of DPD1 into the transport line. The pump 25 will, thereafter, continue to circulate sample liquid and reagent liquid through the measuring loop 1 for about 20 s, in order to mix the reagent DPD1 well into the sample liquid. The content of free chlorine is, thereafter, read off by registering of the tone of colour in the reacted liquid in the measurement cell 26. There is, more specifically, a change to a red tone of colour taking place, which, when the measuring equipment is calibrated, gives a value of the content of free chlorine in the sample liquid.

When the content of free chlorine has been registered accordingly, the total amount of chlorine shall be registered. As a reagent for this measurement can be used DPD4, which is present in the reagent liquid source 11. The method is analogous to what has been described in the foregoing, with the difference that the connection valve 14 is, instead activated, in order to, during a short period, for example 0.25 s, lead DPD4, via the connection line 8 and the connection valve 14 in the transport line and thereafter into the measuring loop 1, as a section of DPD4 corresponding to the intended volume of reagent for which the measuring device is calibrated. The content of bound chlorine can, thereafter, be obtained by subtraction of the content of free chlorine from the content of total amount of chlorine in the bathwater.

For measurement of pH can be used, for example, phenolic red in the reagent liquid source 9. In this case is used the first connection valve 12, which during said time interval, 0.25 s, leads phenolic red into the line section 21 and through the main valve, into the measuring loop 1. The reading off can, in this case, take place by the light detector, which is part of the measuring device, in a manner which is known per se, detecting different tones of red in the member 26, which is part of the measuring loop.

The measuring loop 1 and the transport line 2 is, between each sample-taking, flushed clean by sample liquid from the sample liquid source 5.

I claim:

1. A method in connection with determination of the content of a substance which is solved in a liquid, whereby a measuring device is used, which is arranged to detect the character of a physical magnitude of liquid, which physical magnitude is related to the content of the present substance, when the liquid has been treated with a reagent, characterized in that a volume of the reagent is measured, which volume corresponds to a defined length of a line, in which the reagent is transported, that the measured volume is incorporated in a closed loop in which the measuring device is included, whereby the reagent volume which is incorporated in the measuring loop initially is essentially unmixed with the sample liquid and forms a section in the line of the loop, which for the rest is filled with sample liquid and whereby the length of said section corresponds to or is in direct proportion to said length of the line in which the reagent is transported around in the measuring loop by means of a pump which is included in the measuring loop, until the sample liquid and the reagent are thoroughly mixed in the measuring loop, whereafter the measuring device registers the content of the compound in question.

2. The method according to claim 1, characterized in that said line in which the reagent is measured and transported, is a transport line which does not constitute a part of the measuring loop into which the measured volume of reagent is incorporated.

3. The method according to claim 2, characterized in that said section of reagent is drawn into the measuring loop by means of the pump which is included in the measuring loop, whereby the transport line is connected to the measuring loop, which hereby is open, and to a sample liquid source, and that the measuring loop is closed when said section of reagent has been drawn into the measuring loop.

4. The method according to claim 3, characterized in that the measuring loop first is filled with sample liquid which is drawn into the open measuring loop by means of the pump in the measuring loop, whereby the transport line is connected to the sample liquid source, that the transport line is thereafter connected to a reagent source during a time interval (t) which at a given flow velocity (Q) in the transport line, gives a desired reagent volume V=Q·t, where Q=the flow velocity in the transport line and t=the time during which the transport line is connected to the reagent source, that the transport line thereafter is connected to the sample liquid source, and that sample liquid thereafter is, once again, drawn into the measuring loop in one end of it, at the same time as sample liquid leaves the measuring loop in the other end, until the reagent section has been drawn into the measuring loop and this has been closed.

5. Equipment for measurement of the content of a substance which is solved in a liquid, characterized by a measuring loop in which there is a pump and a member which is part of a measuring device which detects the character of a physical magnitude, which is related to the content of the present substance in the liquid, when this has been treated with a reagent, a transport line with at least a first valve for discretionary connection of the transport line to a sample liquid source and to a reagent source, and a main valve which is switchable between a first position, where the measuring loop is connected to the transport line and to a discharge conduit and a second position, in which the measuring line is closed.

6. The equipment according to claim 5, characterized in that said valves are time controlled.

7. The equipment according to claim 5, characterized in that the transport line includes several valves, which are connected in cascade, for discretionary connection of the transport line to a corresponding number of reagent liquid sources.

8. The equipment according to claim 5, characterized in that the measuring device is a photometrically operating measuring device.

* * * * *